US012152261B2

(12) United States Patent
Dekker

(10) Patent No.: US 12,152,261 B2
(45) Date of Patent: Nov. 26, 2024

(54) METHOD FOR REDUCING FRUCTAN IN A FOOD PRODUCT WITH AID OF INVERTASE (EC 3.2.1.26)

(71) Applicant: DSM IP Assets B.V., Heerlen (NL)

(72) Inventor: Petrus Jacobus Theodorus Dekker, Echt (NL)

(73) Assignee: DSM IP Assets B.V., Heerlen (NL)

( * ) Notice: Subject to any disclaimer, the term of this patent is extended or adjusted under 35 U.S.C. 154(b) by 542 days.

(21) Appl. No.: 17/431,617

(22) PCT Filed: Feb. 18, 2020

(86) PCT No.: PCT/EP2020/054135
§ 371 (c)(1),
(2) Date: Aug. 17, 2021

(87) PCT Pub. No.: WO2020/169545
PCT Pub. Date: Aug. 27, 2020

(65) Prior Publication Data
US 2022/0073893 A1 Mar. 10, 2022

(30) Foreign Application Priority Data

Feb. 19, 2019 (EP) ..................................... 19158094

(51) Int. Cl.
| | |
|---|---|
| *C12N 9/24* | (2006.01) |
| *A21D 8/04* | (2006.01) |
| *A21D 13/062* | (2017.01) |
| *A23L 2/84* | (2006.01) |
| *A23L 7/104* | (2016.01) |
| *A23L 29/00* | (2016.01) |
| *A23L 33/00* | (2016.01) |
| *A23L 33/125* | (2016.01) |

(52) U.S. Cl.
CPC ........... *C12N 9/2402* (2013.01); *A21D 8/042* (2013.01); *A21D 13/062* (2013.01); *A23L 2/84* (2013.01); *A23L 7/107* (2016.08); *A23L 29/06* (2016.08); *A23L 33/125* (2016.08); *A23L 33/40* (2016.08); *C12Y 302/01007* (2013.01); *C12Y 302/01026* (2013.01); *A23V 2002/00* (2013.01)

(58) Field of Classification Search
CPC .......... A23L 29/06; A23L 7/107; A23L 33/40; A23L 33/125; A23L 2/84; A21D 8/042; A21D 13/062; C12N 9/2402; A23V 2002/00
See application file for complete search history.

(56) References Cited

U.S. PATENT DOCUMENTS

| | | | | |
|---|---|---|---|---|
| 2005/0112612 A1* | 5/2005 | Klaenhammer | ... | A23C 19/0323 435/320.1 |
| 2006/0115467 A1* | 6/2006 | Pangborn | ........... | A61K 38/4813 424/94.2 |
| 2011/0129572 A1* | 6/2011 | Meier | ..................... | A21D 8/042 426/64 |
| 2011/0149572 A1 | 6/2011 | Yu-Chow | | |
| 2011/0150855 A1* | 6/2011 | Joh | ......................... | A23L 29/06 435/193 |
| 2020/0255813 A1* | 8/2020 | Zimmerman | ........... | C12P 19/14 |

FOREIGN PATENT DOCUMENTS

| | | | |
|---|---|---|---|
| CN | 102884198 | A | 1/2013 |
| EP | 2271220 | B1 | 12/2015 |
| EP | 3266318 | A1 | 1/2018 |
| GB | 2465814 | * | 2/2010 |
| WO | 2011141175 | A1 | 11/2011 |
| WO | 2017/220864 | A1 | 12/2017 |

OTHER PUBLICATIONS

Fructanase Mixture (liquid). 2023. https://www.megazyme.com/fructanase-mixture-purified-liquid.*
Muir et al., "Gluten-free and low-Fodmap sourdoughs for patients with coeliac disease and irritable bowel syndrome: A clinical perspective," International Journal of Food Microbiology, 2019, vol. 290, pp. 237-246.
Nilsson et al., "Cereal Fructans: Hydrolysis by Yeast Invertase In Vitro and During Fermentation," Journal of Cereal Science, 1987, vol. 6, pp. 53-60.
Skodje et al., "Fructan, Rather Than Gluten, Induces Symptoms in Patients With Self-Reported Non-Celiac Gluten Sensitivity," Gastroenterology, 2018, vol. 154, pp. 529-539.
Struyf et al., "*Saccharomyces cerevisiae* and *Kluyveromyces marxianus* Cocultures Allow Reduction of Fermentable Oligo-, Di-, and Monosaccharides and Polyols Levels in Whole Wheat Bread," Journal of Agricultural and Food Chemistry, Sep. 22, 2017, vol. 65, No. 39, pp. 8704-8713.
Yun et al., "Fructooligosaccharides-occurrence, preparation, and application," Enzyme and Microbial Technology, Aug. 1996, vol. 19, pp. 107-117.
International Search Report received in international application No. PCT/EP2020/054135, mailed Mar. 23, 2020, 32 pages.
Verspreet et al., "Maximizing the Concentrations of Wheat Grain Fructans in Bread by Exploring Strategies To Prevent Their Yeast (*Saccharomyces cerevisiae*)-Mediated Degradation," J. Agric. Food Chem, 2013, vol. 61, pp. 1397-1404.

* cited by examiner

*Primary Examiner* — Anthony J Weier

(74) *Attorney, Agent, or Firm* — McBee Moore & Vanik, IP, LLC

(57) ABSTRACT

The present invention relates to a method for reducing fructan in a fructan-containing food product, including adding an invertase belonging to enzyme classification EC 3.2.1.26 to the food product, and incubating the food product with the invertase, wherein fructan in the fructan-containing food product is hydrolysed. The invention further relates to the use of an invertase belonging to enzyme classification EC. 3.2.1.26 for the preparation of a medicament or a dietary supplement for the treatment of a person suffering from irritable bowel syndrome. Invertase (EC 3.2.1.26) may optionally by further combined with inulinase (EC3.2.1.7) and/or beta-fructosidase (EC 3.2.1.80).

11 Claims, No Drawings

METHOD FOR REDUCING FRUCTAN IN A FOOD PRODUCT WITH AID OF INVERTASE (EC 3.2.1.26)

CROSS-REFERENCE TO RELATED APPLICATIONS

This application is the National Stage entry of International Application No. PCT/EP2020/054135, filed 18 Feb. 2020, which claims priority to European Patent Application No. 19158094.3, filed 19 Feb. 2019.

BACKGROUND

Field

The present invention relates to a method for reducing fructan in a food product.

Description of Related Art

Fructan, such as inulin and levan, is present in several plants, such as cereals, for instance wheat, rye and barley and in onions, garlic, or artichokes. Fructan is considered to be beneficial to the health acting as a prebiotic, but at the same time fructan, such as fructan having a degree of polymerisation (DP) of DP3 to DP5 and being part of the Fermentable Oligo-, Di, Monosaccharides and Polyols (FODMAPS), are considered to contribute to symptoms in patients suffering from irritable bowel syndrome (IBS).

Several studies have been performed on the hydrolysis of fructan.

EP2271220B1 discloses a method for reducing fructan in a dough or a baked product using an inulinase EC 3.2.1.7 and/or a fructan beta-fructosidase, EC 3.2.1.80 with the aim to increase softness of baked products. Inulinase and fructan beta-fructosidase disclosed in EP2271220B1 degrade fructan (inulin and levan) into short chain fructo-oligosaccharides (scFOS) and fructose.

Nilsson et al (1987), J. of Cereal Science 6, 53-60, discloses that invertase from *Saccharomyces cerevisiae* hydrolysed short chain fructan with a DP3 to DP5. Nilsson et al (1987), J. of Cereal Science 6, 53-60, and Verspreet et al. (2013), J. Agric. Food Chem. 61, 1397-1404 disclose that fructan was degraded during dough fermentation by *Saccharomyces cerevisiae* which exhibited invertase activity. The amount of fructan that was hydrolysed was dependent on the yeast type used.

EP 3 266 318 discloses the preparation of sugar-free bread from dough to which inulin (fructan)s, inulinase (EC 3.2.1.7 and EC 3.2.1.80) and invertase (EC 3.2.1.26) were added. The inulin (fructan) that was added to the dough was degraded into sweet-tasting sugars after addition of all three enzymes, and addition of extra sugar was no longer required.

WO2017/220864 discloses an enzyme (SEQ ID NO: 1 in WO2017/220864) isolated from *Lactobacillus* crispatus that is capable of degrading fructan. The enzyme can be used in food products, such as baked products or fructan comprising vegetables low in fructan suitable for a low-FODMAP diets.

There is a need for an improved method for reducing fructan in food products, such as non-fermented food products.

SUMMARY

The present invention relates to a method for reducing an amount of fructan in a fructan-containing food product, comprising adding an invertase belonging to enzyme classification EC 3.2.1.26 (beta-fructofuranosidase) to the food product, and incubating the food product with the invertase, wherein fructan in the fructan-containing food product is hydrolysed.

Also disclosed herein is the use of an invertase for the preparation of a medicament or a dietary supplement for the treatment of a person suffering from irritable bowel syndrome.

DETAILED DESCRIPTION

The present invention relates to a method for reducing an amount of fructan in a fructan-containing food product, comprising adding an invertase belonging to enzyme classification EC 3.2.1.26 (beta-fructofuranosidase) to the food product, and incubating the food product with the invertase, wherein fructan in the fructan-containing food product is hydrolysed.

Surprisingly, it was found that by adding an invertase belonging to enzyme classification EC 3.2.1.26 and incubating the food product with the invertase in a method as disclosed herein an amount of at least 50% of the fructan having a degree of polymerisation (DP) of DP3, DP4 and/or DP5 originally present in the food product and/or intermediate form of the food product is hydrolysed, preferably an amount of at least 60%, 70%, 80%, 90%, or 95% of the fructan having DP3, DP4, and/or DP5 originally present in the food product or intermediate form of the food product is hydrolysed, or all fructan having a DP3, DP4 and/or DP5 originally present in the food product or intermediate form of the food product is hydrolysed in a method as disclosed herein. It was found that a fructan-containing food product produced in method as disclosed herein surprisingly gives less discomfort to a person suffering from irritable bowel syndrome as compared to a fructan-containing food product to which no invertase EC 3.2.1.26 is added.

Degree of polymerisation (DP) is defined herein as the number of monomeric units. For instance, fructan having a DP3 comprises 3 units of fructo-monosaccharides.

Accordingly, a method as disclosed herein comprises reducing an amount of at least 50% of fructan having DP3, DP4, and/or DP5 originally present in the food product, preferably reducing at least 60%, 70%, 80%, 90%, or 95% of the fructan having DP3, DP4, and/or DP5 originally present in the food product and/or intermediate form of the food product. A method as disclosed herein may comprise reducing all or 100% of the fructan having DP3, DP4 and/or DP5 originally present in the food product and/or or intermediate form of the food product.

Examples of fructo-oligosaccharides (fructan fractions) having DP3 are 1-kestose, 6-kestose, and examples or fructo-oligosaccharides having DP4 are nystose, neo-kestose and/or bifurcose, and examples of fructo-oligosaccharides having DP5 are different forms of kestopentaose like e.g. fructosylnystose.

The invertase may be added to the food product in an amount from 0.2 to 2500 SU/gram food product, for instance 2 to 2000 SU/gram food product, for instance, from 5 to 1000 SU/gram food product, such as from 10 to 500 SU/gram food product, such as from 20 to 400 SU/gram food product, such as from 50 to 300 SU/gram food product, such as from 100 to 200 SU/gram food product. Invertase activity is measured according to the Invertase Sumner Unit (SU) activity method described in the Food Chemical Codex (FCC 6, US Pharmacopeial Convention, Rockville MD., p1123-1124).

Invertase that is added to a food product as disclosed herein belongs to enzyme classification EC 3.2.1.26 and is also called beta-fructofuranosidase or beta-D-fructofuranoside fructohydrolase. Invertase may be derived from any suitable microorganism, such as fungi, yeast or bacteria, for instance *Aspergillus* sp, for instance *A. fumigatus, A. niger, Fusarium oxysporum,* or *Saccharomyces cerevisiae.* Invertase as disclosed herein may be derived from *Saccharomyces cerevisiae.* A commercial product comprising invertase EC 3.2.1.26 is Maxinvert® available from DSM Food-Specialties, the Netherlands.

The invertase may be added to the food product, or during preparation of a food product in any suitable manner, for instance by mixing the invertase with suitable ingredients for the preparation of the food product. Adding invertase to the food product may comprise adding invertase to an intermediate form of the food product. An intermediate form of a food product may be a dough, a batter or a mash. For instance, invertase may be added to premix or a dough for the preparation of a baked product, or a mash for the preparation of beer such as a non- or low-alcohol beer.

A method for reducing an amount of fructan in a fructan-containing food product comprises preparing a food product as disclosed herein. For instance, a method as disclosed herein comprises preparing a dough, or a batter and baking or drying the dough or batter at a suitable temperature depending on the food product to be prepared.

Dough is usually a mixture of (cereal) flour, water and optionally salt. Usually, dough is firm enough to knead or roll. The dough may be fresh, frozen, prepared or parbaked. For leavened products primarily baker's yeast is used and optionally chemical leavening compounds can be used, such as a combination of an acid (generating compound) and bicarbonate. In the scope of the present disclosure, cereals comprising fructan from which flour can be made include wheat, rye, barley or spelt. The term dough herein also includes a batter. A batter is a semi-liquid mixture, being thin enough to drop or pour from a spoon, of one or more flours combined with liquids such as water, milk or eggs used to prepare various foods, including cake.

A pre-mix as defined herein is a mix of baking agents, generally including flour, starch, maltodextrin and/or salt, which may be used not only in industrial bread-baking plants/facilities, but also in retail bakeries. A pre-mix as disclosed herein may comprise an invertase belonging to enzyme classification EC 3.2.1.26. A premix as disclosed herein may comprise further enzymes such as lipases and amylases and may also comprise an inulinase belonging to enzyme classification EC 3.2.1.7 and/or a fructan beta-fructosidase belonging to enzyme classification EC 3.2.1.80.

The invertase may be added at any suitable step during the preparation of beer such as low-alcohol or non-alcohol beer, which can be prepared by methods known in the art. Usually a process for preparing beer, including low- and non-alcohol beer comprises preparing a mash, separating wort from the mash and boiling of the wort. Preparing a mash in a process as disclosed herein may comprise preparing a mash from a grist of unmalted cereals, from malted cereals or from a mixture of malted and unmalted cereals. A grist as used herein can also be a malt. Examples of cereals from which a mash and subsequently beer can be prepared are barley and wheat.

Mashing, i.e. the process for preparing a mash, typically involves pauses (rests) at certain temperatures, for instance a pause at 43 to 51° C., a pause at 62 to 65° C., a pause at 72 to 74° C. and/or a pause at 77-78° C. After boiling of the wort the wort is usually filtered and yeast can be added for fermenting the wort. For low-alcohol beer the wort may be fermented shortly or in limited fermentation known in the art. The invertase may be added to the mash, to the wort before or after wort boiling or during fermentation. The wort can be concentrated to malt extract or dried. Dried malt extract can be used in e.g. malt drinks.

Incubating the food product with invertase may comprise incubating an intermediate form of the food product with the invertase. Incubating may be performed in any suitable manner. Incubating a food product or an intermediate form of the food product with the invertase as disclosed herein may comprise incubating the (intermediate form) of the food product with the invertase at a temperature from 15° C. to 80° C., for instance from 20° C. to 70° C., for instance from 25° C. to 65° C., for instance from 30° C. to 60° C., for instance from 35° C. to 55° C., for instance from 40° C. to 50° C. Incubating in a method as disclosed herein comprises incubating during 5 min to 24 hr, for instance from 10 min to 12 hr, for instance from 20 min to 8 hr, for instance from 1 hr to 6 hr. In the event invertase is added during mashing during a process for preparing beer, incubating may comprise the mashing.

Incubating a fructan-containing food product or an intermediate form of the fructan-containing food product in a method as disclosed herein may be performed at any suitable pH, for instance a pH of from 3 to 9, such as a pH from 4 to 8, such as a pH from 5 to 7.

In one embodiment, the method as disclosed herein further comprises adding an inulinase belonging to enzyme classification EC 3.2.1.7 and/or a fructan beta-fructosidase belonging to enzyme classification EC 3.2.1.80 to the food product or to an intermediate form of the food product. These enzymes may be added and incubated in a similar way as disclosed herein above for invertase EC 3.2.1.26. Inulinase EC 3.2.1.7 and fructan beta-fructosidase EC 3.2.1.80 may be produced by fermentation of *Aspergillus niger.* A commercial product comprising these two enzymes is Fructozyme® L available from Novozymes A/S.

In one embodiment, a fructan-containing food product as disclosed herein is a food product comprising cereal material comprising fructan, for instance cereal material comprising rye, wheat barley or spelt, or other material comprising fructan such as onion or garlic. A fructan-containing food product does not contain separately added isolated inulin or fructan.

The fructan-containing food product in a method as disclosed herein may be a non-fermented fructan-containing food product. In non-fermented fructan-containing food products no yeast and/or no bacteria such as lactic acid bacteria are added to the fructan-containing food product or intermediate form of the fructan-containing food product such as dough or batter. Accordingly, non-fermented food products are food products wherein no yeast and/or bacteria have been added during preparation of the food product, or food products that do not comprise added yeast and/or do not comprise added bacteria such as lactic acid bacteria. Examples of non-fermented fructan-containing food products comprise pasta, noodles, cake, cookies, biscuits, pancake, snack foods, pretzels, tortilla chips, tortilla, non- or low-alcohol beer, malt drinks, onion, or garlic. A food product as disclosed herein may comprise rye, wheat, barley or spelt.

Food products such as pasta, noodles, cake, cookies, biscuits, pancake, snack foods, pretzels, tortilla chips, or tortilla are made according to known methods in the art and usually comprise the preparation of a dough or a batter as disclosed herein above.

Surprisingly, it was found that a fructan-containing food product prepared in a method as disclosed herein gives less discomfort to a person suffering from irritable bowel syndrome as compared to a food product that was prepared without addition of and incubation with an invertase.

In one aspect the present disclosure relates to a fructan-containing food product obtainable by a method as disclosed herein. Also disclosed herein is a fructan-containing food product or an intermediate form of a fructan-containing food product which comprises an invertase belonging to enzyme classification EC 3.2.1.26. A fructan-containing food product or an intermediate form of a fructan-containing food product may further comprise an inulinase belonging to enzyme classification EC 3.2.1.7 and/or a fructan beta-fructosidase belonging to enzyme classification EC 3.2.1.80. A fructan-containing food product may be a non-fermented 25 food product as disclosed herein above. All embodiments disclosed herein above for a method for reducing fructan in a fructan-containing food product are applicable a fructan-containing food product as disclosed herein.

In one embodiment the method as disclosed herein the fructan-containing food product renders less discomfort to a person suffering from irritable bowel syndrome.

In one aspect the present disclosure relates to the use of an invertase for the preparation of a medicament or a dietary supplement for the treatment of a person suffering from irritable bowel syndrome. The invertase in the use as disclosed herein belongs to enzyme classification EC 3.2.1.26. In one embodiment the use of an invertase as disclosed herein further comprises the use of inulinase belonging to enzyme classification EC 3.2.1.7 and/or a fructan beta-fructosidase belonging to enzyme classification EC 3.2.1.80. The medicament and/or dietary supplement prepared herein may comprise an invertase EC 3.2.1.26, and inulinase EC 3.2.1.7.and/or a fructan beta-fructosidase EC 3.2.1.80.

Treatment of a person suffering from irritable bowel syndrome may be performed in any suitable manner for instance the treatment comprises administration of the preparation prior to or with the consumption of a food product.

A medicament and dietary supplement as disclosed herein may be prepared in any suitable form, for instance in a sold form such as a tablet or pill, or a liquid form, which is known to a person skilled in the art.

EXAMPLES

Enzymes

Maxinvert® 200000 MG, invertase from *Saccharomyces cerevisiae* was obtained from DSM Food Specialties, the Netherlands.

Enzyme Activity Assay

Invertase activity was measured according to the Invertase Sumner Unit (SU) activity method described in the Food Chemical Codex (FCC 6, US Pharmacopeial Convention, Rockville MD., p1123-1124).

Analysis and Determination of Fructan

Fructans of different degree of polymerization (DP) in the extract supernatant are analyzed and quantified with high-performance anion-exchange chromatography with pulsed amperometric detection (HPAEC-PAD) as described by Vergauwen et al. (2000) J. Experimental Biology 51, 1261-1266. Column used was a Dionex CarboPac PA100 4×250 mm with a CarboPac guard PA100 4×50 mm as guard column. Mobile phase was A (100% milliQ water); B (500 mM NaOH); D (100 mM NaOH+1 M Na-acetate). Gradient applied was according to the following diagram:

| Time (min) | Flow (ml/min) | % A | % B | % D |
|---|---|---|---|---|
| −15 | 1 | 80 | 20 | 0 |
| 0 | 1 | 80 | 20 | 0 |
| 15 | 1 | 64 | 16 | 20 |
| 20 | 1 | 0 | 0 | 100 |
| 25 | 1 | 0 | 0 | 100 |
| 26 | 1 | 80 | 20 | 0 |

Fructan was clearly separated from glucose, sucrose and maltose with these conditions. The fructan fractions were eluted from the column after:
1-kestose: 8.70 min
Neokestose: 10.19 min
Nystose: 10.39 min
Bifurcose: 10.78 min
Other fructan DP4: 10.8-11.5 min
Fructan DP5: 11.5-12.1 min
Fructan DP6: 12.1-13.0 min
Fructan DP7: 13.0-14.5 min
Fructan DP8: 14.5-16.0 min
Fructan DP9: 16.0-17.2 min
Fructan DP10: 17.2-17.9 min
Fructan >DP10: 17.9-19.0
All fructan DP3 to DP10 and >DP10 were quantified relative to the area under the peak of a known amount of 1-kestose.

Example 1: Hydrolysis of Fructan from Wheat Flour into Glucose and Fructose

Dough samples are prepared by mixing 1 kg regular wheat flour with 500 g water and 10 g salt. The mix is divided into 10 pieces of equal weight and 0, 2, 10, 20, 40, 100, 200, 400, 1000 or 2000 SU of Maxinvert® 200000 MG (DSM Food Specialties) per gram dough is added. Knead the dough into a smooth ball. Let it rest at 30° C. for 2 hr and take dough samples immediately after kneading and after 15, 30, 60, 90, and 120 minutes.

Soluble saccharides are extracted from the dough samples using the method described in Verspreet et al (J. Agric. Food Chem. 2013, 61, 1397-1404). Dough samples are immediately frozen using liquid nitrogen, lyophilized, and ground into a powder. The lyophilized dough powders (50 mg) are heated in ethanol (1.0 mL, 90° C.) until all added ethanol is evaporated to inactivate yeast invertase. Samples are extracted with hot water for 60 min (15 mL, 80° C.). Supernatant is collected for fructan analysis.

Example 2: Hydrolysis of Fructan in Pasta Dough

Dough samples are prepared by mixing 300 gram Tipo '00' wheat flour, 300 gram Farina di Semola and 6 large eggs, 6 gram salt, and 3 tablespoons of olive oil and 2-2000 SU/g of Maxinvert® is added or no enzyme addition. If needed, add some water to the mixture. Knead into a smooth dough in a kitchen machine for 5 minutes, cover with plastic foil and let it rest for minimally 30 minutes at room temperature. Pasta is formed from the dough using a regular pasta machine. The fresh pasta is boiled in salted water before consumption.

Example 3: Hydrolysis of Fructan in Mashing

Lab scale mashing trials are performed in a mashing bath (Lochner Labor technik, Germany). 80 gram of milled standard EBC malt is used in 200 ml of water. The mash is step-wise heated as shown in Table 1. The mashes are stirred continuously at 100 rpm during the mashing process. At the end of the mashing the mash 1s filtered over a filter paper (Macherey-Nagel, MN614 ¼, 320 mm diameter). The filtrate is called the wort.

Maxinvert® 200000 MG (2-2000 SU/g) is added to the mash at the start of preparing a mash or to the wort before wort boiling.

Samples are taken from the wort and analysed for the presence of fructans as disclosed above.

TABLE 1

Mashing scheme

| Time from start (min) | Temperature (° C.) |
|---|---|
| 0 | 50 |
| 15 | 50 |
| 28 | 63 |
| 43 | 63 |
| 55 | 75 |
| 70 | 75 |
| 73 | 78 |
| 78 | 78 |

The resulting wort can be used to make low alcohol beer or alcohol-free beer e.g. in a process with limited fermentation e.g. at low temperature e.g. below 10° C., preferable below 4° C. more preferable around 0° C. for a limited time, e.g. 24 hours.

Example 4: Effect of Fructan Hydrolysis on Intestinal Discomfort

A trial is conducted on a test panel of 20 volunteers each of whom suffer from the symptoms of IBS. All members of the panel follow a low FODMAP diet before and during the trial period. During the trial period the volunteers receive a food or beverage containing minimally 2 g fructan per serving with or without the consumption of a dietary supplement comprising invertase.

In a separate trial, volunteers receive a food or beverage containing minimally 2 g fructan per serving, or the similar food or beverage treated with invertase according to a preparation method as disclosed in Examples 1 to 3.

The amount of hydrogen in exhaled breath (ppm) is measured each hour for up to 8 hours after the meal. Various gastrointestinal symptoms (pain, bloating, flatulence, diarrhea, nausea etc.) are recorded during this period.

In the first period volunteers receive the food either untreated or treated with the enzyme on a daily basis. After a washout period they receive the food they have not received in the first period. Volunteers will have less complaints with the enzyme-treated as compared to untreated food.

Example 5: Hydrolysis of Fructan in Dough

Wheat flour (Ibis: Meneba, Rotterdam, the Netherlands) was used to make dough. 100% flour, 2% salt and 62% water, plus 0, 2, 20, 200 or 2000 SU/g flour of Maxinvert 200000 MG, were first kneaded by hand followed kneading using a Hobart mixer on speed 2 for 6 min. The kneaded doughs were divided into pieces of ~10 gram each and stored in centrifuge tubes. All tubes were incubated at 30° C. for 15, 30, 60 or 120 minutes, after which doughs were frozen by addition of liquid nitrogen. Each frozen dough was lyophilized and ground into powders. For extraction of the soluble sugars in the dough powder, 200 mg of powder was incubated in 10 ml of water at 90° C. for 60 mins. 5 ml of the sample was centrifuged at 14,000 rpm for 5 minutes after which the supernatant was filtered via a 0.2 µm filter, and the filtrate was used for fructan detection with HPAEC-PAD as described above.

Total fructan content of wheat flour measured using the HPAEC-PAD method in this experiment is ~0.70% (w/w). The results in Table 2 show that incubation of flour with invertase (Maxinvert) reduced the content of all fructans for up to 90%. No significant additional fructan peaks appeared during the incubation, indicating a full conversion of fructan into mono-saccharides. Residual material after incubation at the neokestose peak area may represent a non-fructan oligosaccharide that is resistant to the action of Maxinvert.

Example 6: Hydrolysis of Fructan in Pasta Dough

Hard wheat semolina flour made by De Cecco (De Cecco Semola di grano duro rimacinata) was used to make pasta dough. 100% flour, 40% whole egg, 8.3% olive oil, 16.7% water, plus 0, 2, 20, 200 or 2000 SU/g flour of Maxinvert 200000 MG, were first kneaded by hand followed by kneading using a Hobart mixer on speed 2 for 4 mins. The kneaded doughs were divided into ~10 gram of dough pieces each and stored in centrifuge tubes. All tubes were incubated at 22° C. for 30 minutes, after which doughs were frozen by addition of liquid nitrogen. Each frozen dough was lyophilized and ground into powders. For extraction of the soluble sugars in the dough powder, 200 mg of powder was incubated in 10 ml of water at 90° C. for 60 mins. 5 ml of the sample was centrifuged at 14,000 rpm for 5 minutes after which the supernatant was filtered via a 0.2 µm filter, and the filtrate was used for fructan detection with HPAEC-PAD as described above.

Total fructan content of wheat flour measured using the HPAEC-PAD method in this experiment is ~0.85% (w/w). The amount of small fructans (DP3-6) is clearly higher, and the high DP fructans are less abundant, in the pasta flour compared to the wheat flour used in the experiment of Example 5.

The results in Table 3 show that incubation of the flour with invertase (Maxinvert) reduces the content of all fructans up to 94%. No significant additional fructan peaks appeared during the incubation, indicating a full conversion of fructan into mono-saccharides.

TABLE 2

Fructan content of the wheat flour (Ibis) used for making dough with and varying amounts of Maxinvert and different incubation times.

| SU/g Maxinvert | min Time | mg/g 1-kestose | mg/g nystose | mg/g neokestose | mg/g bifurcose | mg/g DP4 | mg/g DP5 | mg/g DP6 | mg/g DP7 | mg/g DP8 | mg/g DP9 | mg/g DP10 | mg/g >DP10 | mg/g total |
|---|---|---|---|---|---|---|---|---|---|---|---|---|---|---|
| 0 | 15 | 0.55 | 0.10 | 2.36 | 0.36 | 0.62 | 0.30 | 0.40 | 0.31 | 0.31 | 0.26 | 0.26 | 1.23 | 7.06 |
| 0 | 30 | 0.48 | 0.11 | 2.06 | 0.32 | 0.50 | 0.29 | 0.41 | 0.27 | 0.29 | 0.23 | 0.28 | 1.16 | 6.41 |
| 0 | 60 | 0.56 | 0.11 | 2.53 | 0.42 | 0.60 | 0.37 | 0.51 | 0.33 | 0.37 | 0.27 | 0.32 | 1.36 | 7.74 |

TABLE 2-continued

Fructan content of the wheat flour (Ibis) used for making dough with and varying amounts of Maxinvert and different incubation times.

| SU/g Maxinvert | min Time | mg/g 1-kestose | mg/g nystose | mg/g neokestose | mg/g bifurcose | mg/g DP4 | mg/g DP5 | mg/g DP6 | mg/g DP7 | mg/g DP8 | mg/g DP9 | mg/g DP10 | mg/g >DP10 | mg/g total |
|---|---|---|---|---|---|---|---|---|---|---|---|---|---|---|
| 0 | 120 | 0.51 | 0.10 | 2.13 | 0.34 | 0.49 | 0.37 | 0.48 | 0.31 | 0.33 | 0.25 | 0.31 | 1.16 | 6.79 |
| 2 | 15 | 0.54 | 0.11 | 2.36 | 0.36 | 0.61 | 0.25 | 0.47 | 0.35 | 0.35 | 0.28 | 0.34 | 1.29 | 7.31 |
| 2 | 30 | 0.55 | 0.12 | 2.18 | 0.34 | 0.55 | 0.26 | 0.46 | 0.33 | 0.35 | 0.27 | 0.33 | 1.29 | 7.01 |
| 2 | 60 | 0.52 | 0.12 | 2.26 | 0.35 | 0.57 | 0.26 | 0.48 | 0.33 | 0.35 | 0.28 | 0.35 | 1.21 | 7.10 |
| 2 | 120 | 0.35 | 0.10 | 1.79 | 0.24 | 0.46 | 0.16 | 0.37 | 0.29 | 0.30 | 0.25 | 0.30 | 1.08 | 5.67 |
| 20 | 15 | 0.32 | 0.10 | 1.61 | 0.21 | 0.47 | 0.10 | 0.36 | 0.31 | 0.25 | 0.24 | 0.30 | 0.99 | 5.27 |
| 20 | 30 | 0.23 | 0.09 | 1.18 | 0.14 | 0.38 | 0.08 | 0.29 | 0.25 | 0.21 | 0.22 | 0.28 | 1.00 | 4.34 |
| 20 | 60 | 0.08 | 0.08 | 0.58 | 0.07 | 0.22 | 0.05 | 0.19 | 0.20 | 0.19 | 0.20 | 0.25 | 0.88 | 2.98 |
| 20 | 120 | 0.01 | 0.03 | 0.33 | 0.03 | 0.07 | 0.06 | 0.06 | 0.12 | 0.13 | 0.17 | 0.21 | 0.97 | 2.20 |
| 200 | 15 | 0.06 | 0.02 | 0.41 | 0.06 | 0.09 | 0.05 | 0.07 | 0.12 | 0.08 | 0.10 | 0.12 | 0.42 | 1.61 |
| 200 | 30 | 0.02 | 0.01 | 0.34 | 0.05 | 0.05 | 0.04 | 0.03 | 0.03 | 0.03 | 0.04 | 0.04 | 0.29 | 0.97 |
| 200 | 60 | 0.00 | 0.01 | 0.30 | 0.03 | 0.03 | 0.04 | 0.02 | 0.03 | 0.03 | 0.03 | 0.03 | 0.25 | 0.79 |
| 200 | 120 | 0.00 | 0.00 | 0.31 | 0.00 | 0.02 | 0.05 | 0.00 | 0.01 | 0.01 | 0.01 | 0.01 | 0.17 | 0.61 |
| 2000 | 15 | 0.00 | 0.00 | 0.34 | 0.03 | 0.06 | 0.02 | 0.03 | 0.05 | 0.02 | 0.01 | 0.01 | 0.16 | 0.72 |
| 2000 | 30 | 0.00 | 0.00 | 0.26 | 0.02 | 0.03 | 0.01 | 0.00 | 0.02 | 0.01 | 0.01 | 0.00 | 0.33 | 0.70 |
| 2000 | 60 | 0.00 | 0.00 | 0.31 | 0.03 | 0.04 | 0.03 | 0.01 | 0.02 | 0.01 | 0.00 | 0.06 | 0.31 | 0.81 |
| 2000 | 120 | 0.00 | 0.00 | 0.27 | 0.00 | 0.02 | 0.05 | 0.01 | 0.01 | 0.04 | 0.00 | 0.03 | 0.20 | 0.64 |

Fructan content of the wheat flour (De Cecco) used for making pasta-dough with and varying amounts of Maxinvert and 30 minutes incubation times.

| SU/g Maxinvert | min Time | mg/g 1-kestose | mg/g nystose | mg/g neokestose | mg/g bifurcose | mg/g DP4 | mg/g DP5 | mg/g DP6 | mg/g DP7 | mg/g DP8 | mg/g DP9 | mg/g DP10 | mg/g >DP10 | mg/g total |
|---|---|---|---|---|---|---|---|---|---|---|---|---|---|---|
| 0 | 30 | 1.79 | 0.27 | 3.32 | 0.18 | 1.24 | 0.57 | 0.50 | 0.10 | 0.10 | 0.05 | 0.08 | 0.30 | 8.50 |
| 2 | 30 | 1.73 | 0.27 | 3.35 | 0.20 | 1.30 | 0.52 | 0.54 | 0.09 | 0.09 | 0.05 | 0.08 | 0.39 | 8.62 |
| 20 | 30 | 1.04 | 0.18 | 2.60 | 0.13 | 1.12 | 0.21 | 0.45 | 0.10 | 0.07 | 0.05 | 0.09 | 0.27 | 6.31 |
| 200 | 30 | 0.01 | 0.01 | 0.15 | 0.02 | 0.16 | 0.03 | 0.06 | 0.04 | 0.03 | 0.03 | 0.11 | 0.00 | 0.66 |
| 2000 | 30 | 0.00 | 0.00 | 0.06 | 0.02 | 0.08 | 0.01 | 0.04 | 0.03 | 0.00 | 0.00 | 0.05 | 0.24 | 0.52 |

Example 7: Hydrolysis of Fructan in Malt Drink

Commercial malt drink (Supermalt—Royal Unibrew A/S) was incubated with 0, 0.4, 4, 40, 400 SU/ml Maxinvert 200000 MG for 30 minutes at 22° C. After the incubation the enzyme was inactivated by heating 2 ml of the solution at 90° C. for 30 minutes. The liquid was filtered via a 0.2 μm filter and used directly for fructan detection via HPAEC-PAD as described above. The results in Table 4 show that when malt drink was incubated with 400 SU/ml invertase (Maxinvert), a reduction of 98-99% of the fructans 1-kestose and nystose was obtained. The elution profile of the larger fructans in malt drink is different from the profile in Example 5 and 6 in wheat flour. This is probably because the main cereal used to produce malt drink is barley.

TABLE 4

Fructan content of Supermalt incubated with varying amounts of Maxinvert for 30 minutes

| SU/ml Maxinvert | min Time | mg/L 1-kestose | mg/L nystose |
|---|---|---|---|
| 0 | 30 | 217 | 82 |
| 0.4 | 30 | 228 | 82 |
| 4 | 30 | 240 | 74 |
| 40 | 30 | 60 | 37 |
| 400 | 30 | 4 | 0.7 |

The invention claimed is:

1. A method for reducing an amount of fructan in a non-fermented fructan-containing food product that does not contain separately added isolated inulin or fructan, the method comprising adding an invertase belonging to enzyme classification EC 3.2.1.26 to the non-fermented fructan-containing food product, and incubating the non-fermented fructan-containing food product with the invertase, thereby producing a hydrolysed food product.

2. The method according to claim 1, wherein the invertase is added in an amount of 2 to 2000 SU/gram food product.

3. The method according to claim 1, wherein the fructan comprises fructan oligosaccharides having a degree of polymerisation of DP3, DP4 and/or DP5.

4. The method according to claim 3, wherein an amount of at least 50% of the fructan oligosaccharides having DP3, DP4 and/or DP5 originally present in the non-fermented fructan-containing food product is hydrolysed.

5. The method according to claim 1, further comprising adding an inulinase EC 3.2.1.7 and/or a fructan beta-fructosidase EC 3.2.1.80 to the non-fermented fructan-containing food product.

6. The method according to claim 1, wherein the non-fermented fructan-containing food product has not been prepared with yeast and/or bacteria.

7. The method according to claim 1, wherein the non-fermented fructan-containing food product is selected from the group consisting of pasta, noodles, cake, cookies, biscuits, pancake, snack foods, pretzels, tortilla chips, tortilla, low- or non-alcohol beer, malt drinks, onion, and garlic.

8. The method according to claim 1, wherein the non-fermented fructan-containing food product comprises wheat, rye, barley or spelt.

9. The method according to claim 1, wherein the hydrolysed food product renders less discomfort to a person suffering from irritable bowel syndrome.

10. A food product obtainable by the method according to claim 3 wherein up to 95% or all of the fructan having DP3, DP4, and/or DP5 originally present in the non-fermented fructan-containing food product is hydrolysed.

11. A non-fermented fructan-containing food product comprising an invertase belonging to enzyme classification EC 3.2.1.26, or an intermediate form of a non-fermented fructan-containing food product comprising an invertase belonging to enzyme classification EC 3.2.1.26, wherein the intermediate form is a food form during or before preparation of the food product.

\* \* \* \* \*